United States Patent
Chang

(10) Patent No.: US 10,349,638 B2
(45) Date of Patent: Jul. 16, 2019

(54) HUMAN ARCAP TRANSGENIC MOUSE

(71) Applicant: Tai-Jay Chang, Taipei (TW)

(72) Inventor: Tai-Jay Chang, Taipei (TW)

(*) Notice: Subject to any disclaimer, the term of this patent is extended or adjusted under 35 U.S.C. 154(b) by 4 days.

(21) Appl. No.: 15/650,073

(22) Filed: Jul. 14, 2017

(65) Prior Publication Data

US 2019/0014756 A1    Jan. 17, 2019

(51) Int. Cl.
| | |
|---|---|
| *A01K 67/027* | (2006.01) |
| *C07K 14/705* | (2006.01) |
| *C12N 15/63* | (2006.01) |
| *C07K 14/72* | (2006.01) |
| *C07K 14/00* | (2006.01) |
| *C12N 15/00* | (2006.01) |

(52) U.S. Cl.
CPC ........ *A01K 67/027* (2013.01); *A01K 67/0275* (2013.01); *C07K 14/705* (2013.01); *C07K 14/721* (2013.01); *C12N 15/63* (2013.01); *A01K 2217/05* (2013.01); *A01K 2217/052* (2013.01); *A01K 2217/206* (2013.01); *A01K 2227/105* (2013.01); *A01K 2267/0331* (2013.01); *C07K 14/00* (2013.01); *C12N 15/00* (2013.01); *C12N 2800/107* (2013.01); *C12N 2830/008* (2013.01)

(58) Field of Classification Search
None
See application file for complete search history.

(56) References Cited

U.S. PATENT DOCUMENTS

| | | |
|---|---|---|
| 6,974,683 B2 | 12/2005 | Chang |
| 7,083,934 B2 | 8/2006 | Chang |
| 2003/0082721 A1 | 5/2003 | Chang |

OTHER PUBLICATIONS

Green, L., J. Immunol. Methods: 1999, vol. 231: pp. 11-23.*
MacDonald, L., et al., PNAS, 2014, vol. 111: p. 5147-5152.*
Albertelli et al "Replacing the Mouse Androgen Receptor with Human Alleles Demonstrates Glutamine Tract Length-Dependent Effects on Physiology and Tumorigenesis in Mice" Molecular Endocrinology vol. 20, pp. 1248-1260, 2006.
Chatterjee et al "Targeted Overexpression of Androgen Receptor with a Liver-Specific Promoter in Transgenic Mice" Proceedings of the National Academy of Sciences USA vol. 93, pp. 728-733, 1996.

* cited by examiner

*Primary Examiner* — Michael D Burkhart
(74) *Attorney, Agent, or Firm* — Cesari and McKenna, LLP

(57) ABSTRACT

A non-human transgenic animal that contains in its genome a nucleic acid encoding human ARCAP operably linked to a liver-specific promoter. The transgenic animal expresses the human ARCAP protein and develops tumors of the liver, spleen, abdomen, or lymph. Also provided is a cell line derived from the non-human transgenic animal expressing the human ARCAP gene. Further provided is a method for producing a transgenic mouse by micro-injecting into a fertilized mouse oocyte a vector that contains a human ARCAP cDNA operably linked to a liver-specific promoter and transferring the micro-injected mouse oocyte into a foster mouse.

11 Claims, 4 Drawing Sheets

Specification includes a Sequence Listing.

Fig. 3

SEQUENCE LISTING

<160> NUMBER OF SEQ ID NOS: 4

<210> SEQ ID NO 1
<211> LENGTH: 3016
<212> TYPE: DNA
<213> ORGANISM: Homo sapiens
<220> FEATURE:
<221> NAME/KEY: CDS
<222> LOCATION: (18)..(2597)

<400> SEQUENCE: 1

```
ccggctcagg cagagcc atg tct cgg ggt ggc tcc tac cca cac ctg ttg         50
                   Met Ser Arg Gly Gly Ser Tyr Pro His Leu Leu
                   1               5                   10 tgg gac gtg agg aaa agg tcc ctc ggg ctg gag gac ccg tcc cgg ctg        98
Trp Asp Val Arg Lys Arg Ser Leu Gly Leu Glu Asp Pro Ser Arg Leu
        15                  20                  25 cgg agt cgc tac ctg gga aga aga gaa ttt atc caa aga tta aaa ctt       146
Arg Ser Arg Tyr Leu Gly Arg Arg Glu Phe Ile Gln Arg Leu Lys Leu
 30                  35                  40 gaa gca acc ctt aat gtg cat gat ggt tgt gtt aat aca atc tgt tgg       194
Glu Ala Thr Leu Asn Val His Asp Gly Cys Val Asn Thr Ile Cys Trp
 45                  50                  55 aat gac act gga gaa tat att tta tct ggc tca gat gac acc aaa tta       242
Asn Asp Thr Gly Glu Tyr Ile Leu Ser Gly Ser Asp Asp Thr Lys Leu
60                  65                  70                  75 gta att agt aat cct tac agc aga aag gtt ttg aca aca att cgt tca       290
Val Ile Ser Asn Pro Tyr Ser Arg Lys Val Leu Thr Thr Ile Arg Ser
                 80                  85                  90 ggg cac cga gca aac ata ttt agt gca aag ttc tta cct tgt aca aat       338
Gly His Arg Ala Asn Ile Phe Ser Ala Lys Phe Leu Pro Cys Thr Asn
             95                 100                 105 gat aaa cag att gta tcc tgc tct gga gat gga gta ata ttt tat acc       386
Asp Lys Gln Ile Val Ser Cys Ser Gly Asp Gly Val Ile Phe Tyr Thr
        110                 115                 120 aac gtt gag caa gat gca gaa acc aac aga caa tgc caa ttt acg tgt       434
Asn Val Glu Gln Asp Ala Glu Thr Asn Arg Gln Cys Gln Phe Thr Cys
    125                 130                 135 cat tat gga act act tat gag att atg act gta ccc aat gac cct tac       482
His Tyr Gly Thr Thr Tyr Glu Ile Met Thr Val Pro Asn Asp Pro Tyr
140                 145                 150                 155 act ttt ctc tct tgt ggt gaa gat gga act gtt agg tgg ttt gat aca       530
Thr Phe Leu Ser Cys Gly Glu Asp Gly Thr Val Arg Trp Phe Asp Thr
                160                 165                 170 cgc atc aaa act agc tgc aca aaa gaa gat tgt aaa gat gat att tta       578
Arg Ile Lys Thr Ser Cys Thr Lys Glu Asp Cys Lys Asp Asp Ile Leu
            175                 180                 185 att aac tgt cga cgt gct gcc acg tct gtt gct att tgc cca cca ata       626
Ile Asn Cys Arg Arg Ala Ala Thr Ser Val Ala Ile Cys Pro Pro Ile
        190                 195                 200 cca tat tac ctt gct gtt ggt tgt tct gac agc tca gta cga ata tat       674
Pro Tyr Tyr Leu Ala Val Gly Cys Ser Asp Ser Ser Val Arg Ile Tyr
    205                 210                 215 gat cgg cga atg ctg ggc aca aga gct aca ggg aat tat gca ggt cga       722
Asp Arg Arg Met Leu Gly Thr Arg Ala Thr Gly Asn Tyr Ala Gly Arg
220                 225                 230                 235 ggg act act gga atg gtt gcc cgt ttt att cct tcc cat ctt aat aat       770
Gly Thr Thr Gly Met Val Ala Arg Phe Ile Pro Ser His Leu Asn Asn
                240                 245                 250 aag tcc tgc aga gtg aca tct ctg tgt tac agt gaa gat ggt caa gag       818
Lys Ser Cys Arg Val Thr Ser Leu Cys Tyr Ser Glu Asp Gly Gln Glu
```

-continued

```
                          255                 260                 265
att ctc gtt agt tac tct tca gat tac ata tat ctt ttt gac ccg aaa    866
Ile Leu Val Ser Tyr Ser Ser Asp Tyr Ile Tyr Leu Phe Asp Pro Lys
            270                 275                 280 gat gat aca gca cga gaa ctt aaa act cct tct gcg gaa gag aga aga    914
Asp Asp Thr Ala Arg Glu Leu Lys Thr Pro Ser Ala Glu Glu Arg Arg
285                 290                 295 gaa gag ttg cga caa cca cca gtt aag cgt ttg aga ctt cgt ggt gat    962
Glu Glu Leu Arg Gln Pro Pro Val Lys Arg Leu Arg Leu Arg Gly Asp
300                 305                 310                 315 tgg tca gat act gga ccc aga gca agg ccg gag agt gaa cga gaa cga   1010
Trp Ser Asp Thr Gly Pro Arg Ala Arg Pro Glu Ser Glu Arg Glu Arg
                    320                 325                 330 gat gga gag cag agt ccc aat gtg tca ttg atg cag aga atg tct gat   1058
Asp Gly Glu Gln Ser Pro Asn Val Ser Leu Met Gln Arg Met Ser Asp
                335                 340                 345 atg tta tca aga tgg ttt gaa gaa gca agt gag gtt gca caa agc aat   1106
Met Leu Ser Arg Trp Phe Glu Glu Ala Ser Glu Val Ala Gln Ser Asn
            350                 355                 360 aga gga cga gga aga tct cga ccc aga ggt gga aca agt caa tca gat   1154
Arg Gly Arg Gly Arg Ser Arg Pro Arg Gly Gly Thr Ser Gln Ser Asp
365                 370                 375 att tca act ctt cct acg gtc cca tca agt cct gat ttg gaa gtg agt   1202
Ile Ser Thr Leu Pro Thr Val Pro Ser Ser Pro Asp Leu Glu Val Ser
380                 385                 390                 395 gaa act gca atg gaa gta gat act cca gct gaa caa ttt ctt cag cct   1250
Glu Thr Ala Met Glu Val Asp Thr Pro Ala Glu Gln Phe Leu Gln Pro
                    400                 405                 410 tct aca tcc tct aca atg tca gct cag gct cat tcg aca tca tct ccc   1298
Ser Thr Ser Ser Thr Met Ser Ala Gln Ala His Ser Thr Ser Ser Pro
                415                 420                 425 aca gaa agc cct cat tct act cct ttg cta tct tct cca gac agt gaa   1346
Thr Glu Ser Pro His Ser Thr Pro Leu Leu Ser Ser Pro Asp Ser Glu
            430                 435                 440 caa agg cag tct gtt gag gca tct gga cac cac aca cat cat cag tct   1394
Gln Arg Gln Ser Val Glu Ala Ser Gly His His Thr His His Gln Ser
445                 450                 455 gat aac aat aat gaa aag ctg agc ccc aaa cca ggg aca ggt gaa cca   1442
Asp Asn Asn Asn Glu Lys Leu Ser Pro Lys Pro Gly Thr Gly Glu Pro
460                 465                 470                 475 gtt tta agt ttg cac tac agc aca gaa gga aca act aca agc aca ata   1490
Val Leu Ser Leu His Tyr Ser Thr Glu Gly Thr Thr Thr Ser Thr Ile
                    480                 485                 490 aaa ctg aac ttt aca gat gaa tgg agc agt ata gca tca agt tct aga   1538
Lys Leu Asn Phe Thr Asp Glu Trp Ser Ser Ile Ala Ser Ser Ser Arg
                495                 500                 505 gga att ggg agc cat tgc aaa tct gag ggt cag gag gaa tct ttc gtc   1586
Gly Ile Gly Ser His Cys Lys Ser Glu Gly Gln Glu Glu Ser Phe Val
            510                 515                 520 cca cag agc tca gtg caa cca cca gaa gga gac agt gaa aca aaa gct   1634
Pro Gln Ser Ser Val Gln Pro Pro Glu Gly Asp Ser Glu Thr Lys Ala
525                 530                 535 cct gaa gaa tca tca gag gat gtg aca aaa tat cag gaa gga gta tct   1682
Pro Glu Glu Ser Ser Glu Asp Val Thr Lys Tyr Gln Glu Gly Val Ser
540                 545                 550                 555 gca gaa aac cca gtt gag aac cat atc aat ata aca caa tca gat aag   1730
Ala Glu Asn Pro Val Glu Asn His Ile Asn Ile Thr Gln Ser Asp Lys
                    560                 565                 570 ttc aca gcc aag cca ttg gat tcc aac tca gga gaa aga aat gac ctc   1778
Phe Thr Ala Lys Pro Leu Asp Ser Asn Ser Gly Glu Arg Asn Asp Leu
```

-continued

| | | |
|---|---|---|
| Phe Thr Ala Lys Pro Leu Asp Ser Asn Ser Gly Glu Arg Asn Asp Leu<br>575 580 585 | | |
| aat ctt gat cgc tct tgt ggg gtt cca gaa gaa tct gct tca tct gaa<br>Asn Leu Asp Arg Ser Cys Gly Val Pro Glu Glu Ser Ala Ser Ser Glu<br>590 595 600 | 1826 | |
| aaa gcc aag gaa cca gaa act tca gat cag act agc act gag agt gct<br>Lys Ala Lys Glu Pro Glu Thr Ser Asp Gln Thr Ser Thr Glu Ser Ala<br>605 610 615 | 1874 | |
| acc aat gaa aat aac acc aat cct gag cct cag ttc caa aca gaa gcc<br>Thr Asn Glu Asn Asn Thr Asn Pro Glu Pro Gln Phe Gln Thr Glu Ala<br>620 625 630 635 | 1922 | |
| act ggg cct tca gct cat gaa gaa aca tcc acc agg gac tct gct ctt<br>Thr Gly Pro Ser Ala His Glu Glu Thr Ser Thr Arg Asp Ser Ala Leu<br>640 645 650 | 1970 | |
| cag gac aca gat gac agt gat gat gac cca gtc ctg atc cca ggt gca<br>Gln Asp Thr Asp Asp Ser Asp Asp Asp Pro Val Leu Ile Pro Gly Ala<br>655 660 665 | 2018 | |
| agg tat cga gca gga cct ggt gat aga cgc tct gct gtt gcc cgt att<br>Arg Tyr Arg Ala Gly Pro Gly Asp Arg Arg Ser Ala Val Ala Arg Ile<br>670 675 680 | 2066 | |
| cag gag ttc ttc aga cgg aga aaa gaa agg aaa gaa atg gaa gaa ttg<br>Gln Glu Phe Phe Arg Arg Arg Lys Glu Arg Lys Glu Met Glu Glu Leu<br>685 690 695 | 2114 | |
| gat act ttg aac att aga agg ccg cta gta aaa atg gtt tat aaa ggc<br>Asp Thr Leu Asn Ile Arg Arg Pro Leu Val Lys Met Val Tyr Lys Gly<br>700 705 710 715 | 2162 | |
| cat cgc aac tcc agg aca atg ata aaa gaa gcc aat ttc tgg ggt gct<br>His Arg Asn Ser Arg Thr Met Ile Lys Glu Ala Asn Phe Trp Gly Ala<br>720 725 730 | 2210 | |
| aac ttt gta atg agt ggt tct gac tgt ggc cac att ttc atc tgg gat<br>Asn Phe Val Met Ser Gly Ser Asp Cys Gly His Ile Phe Ile Trp Asp<br>735 740 745 | 2258 | |
| cgg cac act gct gag cat ttg atg ctt ctg gaa gct gat aat cat gtg<br>Arg His Thr Ala Glu His Leu Met Leu Leu Glu Ala Asp Asn His Val<br>750 755 760 | 2306 | |
| gta aac tgc ctg cag cca cat ccg ttt gac cca att tta gcc tca tct<br>Val Asn Cys Leu Gln Pro His Pro Phe Asp Pro Ile Leu Ala Ser Ser<br>765 770 775 | 2354 | |
| ggc ata gat tat gac ata aag atc tgg tca cca tta gaa gag tca agg<br>Gly Ile Asp Tyr Asp Ile Lys Ile Trp Ser Pro Leu Glu Glu Ser Arg<br>780 785 790 795 | 2402 | |
| att ttt aac cga aaa ctt gct gat gaa gtt ata act cga aac gaa ctc<br>Ile Phe Asn Arg Lys Leu Ala Asp Glu Val Ile Thr Arg Asn Glu Leu<br>800 805 810 | 2450 | |
| atg ctg gaa gaa act aga aac acc att aca gtt cca gcc tct ttc atg<br>Met Leu Glu Glu Thr Arg Asn Thr Ile Thr Val Pro Ala Ser Phe Met<br>815 820 825 | 2498 | |
| ttg agg atg ttg gct tca ctt aat cat atc cga gct gac cgg ttg gag<br>Leu Arg Met Leu Ala Ser Leu Asn His Ile Arg Ala Asp Arg Leu Glu<br>830 835 840 | 2546 | |
| ggt gac aga tca gaa ggc tct ggt caa gag aat gaa aat gag gat gag<br>Gly Asp Arg Ser Glu Gly Ser Gly Gln Glu Asn Glu Asn Glu Asp Glu<br>845 850 855 | 2594 | |
| gaa taataaactc tttttggcaa gcacttaaat gttctgaaat ttgtataaga<br>Glu<br>860 | 2647 | |
| catttattat atttttttct ttacagagct ttagtgcaat tttaaggtta tggttttgg | 2707 | |
| agttttcccc tttttttggg ataacctaac attggtttgg aatgattgtg tgcatgaatt | 2767 | |

-continued

```
tgggagattg tataaaacaa aactagcaga atgttttaa aacttttgc cgtgtatgag    2827 gagtgctaga aaatgcaaag tgcaatattt tccctaacct tcaaatgtgg gagcttggat    2887
caatgttgaa gaataatttt catcatagtg aaaatgttgg ttcaaataaa tttctacact    2947
tgccatttgc atgtttgttg ctttctaatt aaagaaactg gttgttttaa aaaaaaaaa    3007 aaggaattc                                                            3016
```

<210> SEQ ID NO 2
<211> LENGTH: 860
<212> TYPE: PRT
<213> ORGANISM: Homo sapiens

<400> SEQUENCE: 2

```
Met Ser Arg Gly Gly Ser Tyr Pro His Leu Leu Trp Asp Val Arg Lys
1               5                   10                  15

Arg Ser Leu Gly Leu Glu Asp Pro Ser Arg Leu Arg Ser Arg Tyr Leu
            20                  25                  30

Gly Arg Arg Glu Phe Ile Gln Arg Leu Lys Leu Glu Ala Thr Leu Asn
        35                  40                  45

Val His Asp Gly Cys Val Asn Thr Ile Cys Trp Asn Asp Thr Gly Glu
    50                  55                  60

Tyr Ile Leu Ser Gly Ser Asp Asp Thr Lys Leu Val Ile Ser Asn Pro
65                  70                  75                  80

Tyr Ser Arg Lys Val Leu Thr Thr Ile Arg Ser Gly His Arg Ala Asn
                85                  90                  95

Ile Phe Ser Ala Lys Phe Leu Pro Cys Thr Asn Asp Lys Gln Ile Val
            100                 105                 110

Ser Cys Ser Gly Asp Gly Val Ile Phe Tyr Thr Asn Val Glu Gln Asp
        115                 120                 125

Ala Glu Thr Asn Arg Gln Cys Gln Phe Thr Cys His Tyr Gly Thr Thr
    130                 135                 140

Tyr Glu Ile Met Thr Val Pro Asn Asp Pro Tyr Thr Phe Leu Ser Cys
145                 150                 155                 160

Gly Glu Asp Gly Thr Val Arg Trp Phe Asp Thr Arg Ile Lys Thr Ser
                165                 170                 175

Cys Thr Lys Glu Asp Cys Lys Asp Asp Ile Leu Ile Asn Cys Arg Arg
            180                 185                 190

Ala Ala Thr Ser Val Ala Ile Cys Pro Pro Ile Pro Tyr Tyr Leu Ala
        195                 200                 205

Val Gly Cys Ser Asp Ser Ser Val Arg Ile Tyr Asp Arg Arg Met Leu
    210                 215                 220

Gly Thr Arg Ala Thr Gly Asn Tyr Ala Gly Arg Gly Thr Thr Gly Met
225                 230                 235                 240

Val Ala Arg Phe Ile Pro Ser His Leu Asn Asn Lys Ser Cys Arg Val
                245                 250                 255

Thr Ser Leu Cys Tyr Ser Glu Asp Gly Gln Glu Ile Leu Val Ser Tyr
            260                 265                 270

Ser Ser Asp Tyr Ile Tyr Leu Phe Asp Pro Lys Asp Asp Thr Ala Arg
        275                 280                 285

Glu Leu Lys Thr Pro Ser Ala Glu Glu Arg Arg Glu Glu Leu Arg Gln
    290                 295                 300

Pro Pro Val Lys Arg Leu Arg Leu Arg Gly Asp Trp Ser Asp Thr Gly
305                 310                 315                 320

Pro Arg Ala Arg Pro Glu Ser Glu Arg Glu Arg Asp Gly Glu Gln Ser
```

-continued

```
                325                 330                 335
Pro Asn Val Ser Leu Met Gln Arg Met Ser Asp Met Leu Ser Arg Trp
            340                 345                 350
Phe Glu Glu Ala Ser Glu Val Ala Gln Ser Asn Arg Gly Arg Gly Arg
            355                 360                 365
Ser Arg Pro Arg Gly Gly Thr Ser Gln Ser Asp Ile Ser Thr Leu Pro
            370                 375                 380
Thr Val Pro Ser Ser Pro Asp Leu Glu Val Ser Glu Thr Ala Met Glu
385                 390                 395                 400
Val Asp Thr Pro Ala Glu Gln Phe Leu Gln Pro Ser Thr Ser Ser Thr
                405                 410                 415
Met Ser Ala Gln Ala His Ser Thr Ser Ser Pro Thr Glu Ser Pro His
            420                 425                 430
Ser Thr Pro Leu Leu Ser Ser Pro Asp Ser Glu Gln Arg Gln Ser Val
            435                 440                 445
Glu Ala Ser Gly His His Thr His His Gln Ser Asp Asn Asn Asn Glu
            450                 455                 460
Lys Leu Ser Pro Lys Pro Gly Thr Gly Glu Pro Val Leu Ser Leu His
465                 470                 475                 480
Tyr Ser Thr Glu Gly Thr Thr Thr Ser Thr Ile Lys Leu Asn Phe Thr
                485                 490                 495
Asp Glu Trp Ser Ser Ile Ala Ser Ser Ser Arg Gly Ile Gly Ser His
            500                 505                 510
Cys Lys Ser Glu Gly Gln Glu Glu Ser Phe Val Pro Gln Ser Ser Val
            515                 520                 525
Gln Pro Pro Glu Gly Asp Ser Glu Thr Lys Ala Pro Glu Glu Ser Ser
            530                 535                 540
Glu Asp Val Thr Lys Tyr Gln Glu Gly Val Ser Ala Glu Asn Pro Val
545                 550                 555                 560
Glu Asn His Ile Asn Ile Thr Gln Ser Asp Lys Phe Thr Ala Lys Pro
                565                 570                 575
Leu Asp Ser Asn Ser Gly Glu Arg Asn Asp Leu Asn Leu Asp Arg Ser
            580                 585                 590
Cys Gly Val Pro Glu Glu Ser Ala Ser Ser Glu Lys Ala Lys Glu Pro
            595                 600                 605
Glu Thr Ser Asp Gln Thr Ser Thr Glu Ser Ala Thr Asn Glu Asn Asn
            610                 615                 620
Thr Asn Pro Glu Pro Gln Phe Gln Thr Glu Ala Thr Gly Pro Ser Ala
625                 630                 635                 640
His Glu Glu Thr Ser Thr Arg Asp Ser Ala Leu Gln Asp Thr Asp Asp
                645                 650                 655
Ser Asp Asp Asp Pro Val Leu Ile Pro Gly Ala Arg Tyr Arg Ala Gly
            660                 665                 670
Pro Gly Asp Arg Arg Ser Ala Val Ala Arg Ile Gln Glu Phe Phe Arg
            675                 680                 685
Arg Arg Lys Glu Arg Lys Glu Met Glu Glu Leu Asp Thr Leu Asn Ile
            690                 695                 700
Arg Arg Pro Leu Val Lys Met Val Tyr Lys Gly His Arg Asn Ser Arg
705                 710                 715                 720
Thr Met Ile Lys Glu Ala Asn Phe Trp Gly Ala Asn Phe Val Met Ser
                725                 730                 735
Gly Ser Asp Cys Gly His Ile Phe Ile Trp Asp Arg His Thr Ala Glu
            740                 745                 750
```

```
His Leu Met Leu Glu Ala Asp Asn His Val Val Asn Cys Leu Gln
    755                 760                 765

Pro His Pro Phe Asp Pro Ile Leu Ala Ser Ser Gly Ile Asp Tyr Asp
    770                 775                 780

Ile Lys Ile Trp Ser Pro Leu Glu Glu Ser Arg Ile Phe Asn Arg Lys
785                 790                 795                 800

Leu Ala Asp Glu Val Ile Thr Arg Asn Glu Leu Met Leu Glu Thr
                    805                 810                 815

Arg Asn Thr Ile Thr Val Pro Ala Ser Phe Met Leu Arg Met Leu Ala
                820                 825                 830

Ser Leu Asn His Ile Arg Ala Asp Arg Leu Glu Gly Asp Arg Ser Glu
                835                 840                 845

Gly Ser Gly Gln Glu Asn Glu Asn Glu Asp Glu Glu
    850                 855                 860

<210> SEQ ID NO 3
<211> LENGTH: 3340
<212> TYPE: DNA
<213> ORGANISM: Mus musculus
<220> FEATURE:
<221> NAME/KEY: CDS
<222> LOCATION: (218)..(2905)

<400> SEQUENCE: 3
```

| | |
|---|---|
| gagagtatga ggcgagccgt ggcccgggtg cctctccgct cccggggaga aggcgcggcc | 60 |
| gtggctgccg ccctctgagt cgcggcgccg gcgaggcccc ggggcgcgcg catggtgctg | 120 |
| gtgccgctcg ggtgttgatc ggcctgtccc ctccctctct tcccctcccc accccccgcg | 180 |
| gtggtctccc ctttcccacc ccagcccttg cggagcc atg gct cgg agt ggc tcc | 235 |
|                                                             Met Ala Arg Ser Gly Ser | |
| | |

```
                                              Met Ala Arg Ser Gly Ser
                                                1               5 tgc ccg cac ctg ttg tgg gac gtg agg aaa agg tcc ctt ggg ctg gag    283
Cys Pro His Leu Leu Trp Asp Val Arg Lys Arg Ser Leu Gly Leu Glu
        10                  15                  20 gac ccg tcc cgg ctg agg agc cgc tac ctg gga aga aga gaa ttt atc    331
Asp Pro Ser Arg Leu Arg Ser Arg Tyr Leu Gly Arg Arg Glu Phe Ile
    25                  30                  35 caa aga tta aaa ctt gaa gca act tta aat gtg cat gat ggc tgt gtt    379
Gln Arg Leu Lys Leu Glu Ala Thr Leu Asn Val His Asp Gly Cys Val
40                  45                  50 aat aca atc tgt tgg aat gac act gga gaa tat att tta tct ggc tct    427
Asn Thr Ile Cys Trp Asn Asp Thr Gly Glu Tyr Ile Leu Ser Gly Ser
55                  60                  65                  70 gat gac act aaa ctt gta att agt aat cca tac agc aga aag gtt ttg    475
Asp Asp Thr Lys Leu Val Ile Ser Asn Pro Tyr Ser Arg Lys Val Leu
                75                  80                  85 aca acc atc cgt tca ggg cat cga gca aat ata ttt agt gca aag ttt    523
Thr Thr Ile Arg Ser Gly His Arg Ala Asn Ile Phe Ser Ala Lys Phe
        90                  95                  100 ttg ccg tgc aca gat gat aag cag att gtg tct tgc tct gga gat gga    571
Leu Pro Cys Thr Asp Asp Lys Gln Ile Val Ser Cys Ser Gly Asp Gly
    105                 110                 115 gtc ata ttt tat act aac att gag caa gat gca gaa act aac aga cag    619
Val Ile Phe Tyr Thr Asn Ile Glu Gln Asp Ala Glu Thr Asn Arg Gln
120                 125                 130 tgc caa ttt acg tgc cat tat gga act act tat gag att atg act gta    667
Cys Gln Phe Thr Cys His Tyr Gly Thr Thr Tyr Glu Ile Met Thr Val
135                 140                 145                 150
```

-continued

| | | |
|---|---|---|
| cca aac gac cct tac acc ttt ctg tcc tgt ggt gaa gat gga act gtt<br>Pro Asn Asp Pro Tyr Thr Phe Leu Ser Cys Gly Glu Asp Gly Thr Val<br>155                            160                        165 | 715 |
| agg tgg ttt gac aca cgc atc aaa acc agt tgc aca aaa gaa gac tgt<br>Arg Trp Phe Asp Thr Arg Ile Lys Thr Ser Cys Thr Lys Glu Asp Cys<br>                170                        175                    180 | 763 |
| aaa gat gat att tta atc aac tgt agg cgt gct gcc aca tct gtg gct<br>Lys Asp Asp Ile Leu Ile Asn Cys Arg Arg Ala Ala Thr Ser Val Ala<br>              185                      190                    195 | 811 |
| att tgt ccc cca gta cca tat tac ctt gct gtg ggt tgt tct gac agc<br>Ile Cys Pro Pro Val Pro Tyr Tyr Leu Ala Val Gly Cys Ser Asp Ser<br>200                          205                        210 | 859 |
| tca gta cgg att tat gat cgg cga atg ctg ggc aca aga gct aca ggg<br>Ser Val Arg Ile Tyr Asp Arg Arg Met Leu Gly Thr Arg Ala Thr Gly<br>215                          220                        225                    230 | 907 |
| aat tat gca ggc cga gga act act gga atg gtt gct cga ttt ata cct<br>Asn Tyr Ala Gly Arg Gly Thr Thr Gly Met Val Ala Arg Phe Ile Pro<br>                     235                      240                    245 | 955 |
| tct cat ctt agt aac aaa tca tgc aga gtg aca tca ctg tgt tac agt<br>Ser His Leu Ser Asn Lys Ser Cys Arg Val Thr Ser Leu Cys Tyr Ser<br>              250                      255                    260 | 1003 |
| gaa gat ggt caa gag att ctt gtc agt tat tct tca gac tac atc tat<br>Glu Asp Gly Gln Glu Ile Leu Val Ser Tyr Ser Ser Asp Tyr Ile Tyr<br>                265                      270                    275 | 1051 |
| ctt ttt gac ccc aaa gat gat act gca cga gaa ctt aaa act cct tct<br>Leu Phe Asp Pro Lys Asp Asp Thr Ala Arg Glu Leu Lys Thr Pro Ser<br>280                          285                        290 | 1099 |
| gca gag gag agg cga gaa gag tta cga cag cct cca gtt aag cgc ttg<br>Ala Glu Glu Arg Arg Glu Glu Leu Arg Gln Pro Pro Val Lys Arg Leu<br>295                          300                        305                    310 | 1147 |
| aga ctt cgt ggt gat tgg tca gat act ggt ccc aga gca cgg cca gaa<br>Arg Leu Arg Gly Asp Trp Ser Asp Thr Gly Pro Arg Ala Arg Pro Glu<br>                     315                      320                    325 | 1195 |
| agt gaa cga gaa cga gat gga gag caa agt ccc aat gtg tca ctg atg<br>Ser Glu Arg Glu Arg Asp Gly Glu Gln Ser Pro Asn Val Ser Leu Met<br>              330                      335                    340 | 1243 |
| cag aga atg tct gat atg tta tca agg tgg ttt gaa gaa gca agt gaa<br>Gln Arg Met Ser Asp Met Leu Ser Arg Trp Phe Glu Glu Ala Ser Glu<br>345                          350                        355 | 1291 |
| gtt gca caa agc aac aga gga aga gga aga cct cgg ccc aga ggt gga<br>Val Ala Gln Ser Asn Arg Gly Arg Gly Arg Pro Arg Pro Arg Gly Gly<br>              360                      365                    370 | 1339 |
| aca aat cag cca gat gtt tca act ctt cct acg gtt cca tca agt cct<br>Thr Asn Gln Pro Asp Val Ser Thr Leu Pro Thr Val Pro Ser Ser Pro<br>375                          380                        385                    390 | 1387 |
| aat ttg gaa gtg tgt gaa act gca atg gat gta gac atg cca gct gca<br>Asn Leu Glu Val Cys Glu Thr Ala Met Asp Val Asp Met Pro Ala Ala<br>                     395                      400                    405 | 1435 |
| ctt ctt cag cct tct aca tcc tct aca gat cca gtt cag gct cag gca<br>Leu Leu Gln Pro Ser Thr Ser Ser Thr Asp Pro Val Gln Ala Gln Ala<br>              410                      415                    420 | 1483 |
| gcc aca gcc gcc ata gaa agc cct cgt tcc agc tcg ttg ctg tct tgc<br>Ala Thr Ala Ala Ile Glu Ser Pro Arg Ser Ser Ser Leu Leu Ser Cys<br>425                          430                        435 | 1531 |
| cca gac agt gaa ccg agg cag tct gtt gag gcg tct gga cac cat gca<br>Pro Asp Ser Glu Pro Arg Gln Ser Val Glu Ala Ser Gly His His Ala<br>440                          445                        450 | 1579 |
| cat cat cag tca gat tct cct tct tct gtg gtt aac aaa cag ctg gga<br>His His Gln Ser Asp Ser Pro Ser Ser Val Val Asn Lys Gln Leu Gly<br>455                          460                        465                    470 | 1627 |

```
                                                       -continued tcc atg tca ctt gat gag caa cag gat aac agt aat gag agg ctg agc    1675
Ser Met Ser Leu Asp Glu Gln Gln Asp Asn Ser Asn Glu Arg Leu Ser
            475                 480                 485 ccc aaa cca ggg aca ggt gaa ccc gtt tta agt ttg cac tac agc aca    1723
Pro Lys Pro Gly Thr Gly Glu Pro Val Leu Ser Leu His Tyr Ser Thr
        490                 495                 500 gaa gga aca act aca agc aca ata aaa ctg aac ttt aca gat gaa tgg    1771
Glu Gly Thr Thr Thr Ser Thr Ile Lys Leu Asn Phe Thr Asp Glu Trp
    505                 510                 515 agc agt aca gcc tca agt tcc aga gga aat ggg agc cat tgc aaa tct    1819
Ser Ser Thr Ala Ser Ser Arg Gly Asn Gly Ser His Cys Lys Ser
520                 525                 530 gag ggt cag gaa gaa tgc ttg gtc cct ccg agc tct gtg cag cca ccg    1867
Glu Gly Gln Glu Glu Cys Leu Val Pro Pro Ser Ser Val Gln Pro Pro
535                 540                 545                 550 gaa gga gac agt gaa aca aga gct cct gaa gaa cta tca gag aaa gga    1915
Glu Gly Asp Ser Glu Thr Arg Ala Pro Glu Glu Leu Ser Glu Lys Gly
                555                 560                 565 aca ctt cca gaa aac ctc act caa aac cag ata gat aca gca caa ctt    1963
Thr Leu Pro Glu Asn Leu Thr Gln Asn Gln Ile Asp Thr Ala Gln Leu
            570                 575                 580 gat aac ttc cca gct gag cca ttg gat tct aac tca gga gag aag aat    2011
Asp Asn Phe Pro Ala Glu Pro Leu Asp Ser Asn Ser Gly Glu Lys Asn
        585                 590                 595 aac cca agt cag gac agc cct tgt ggg ctt cca gaa gaa ggc act ttg    2059
Asn Pro Ser Gln Asp Ser Pro Cys Gly Leu Pro Glu Glu Gly Thr Leu
    600                 605                 610 tct gaa aca gac agg gag act tgt gag cag gcc agc act gag agt gct    2107
Ser Glu Thr Asp Arg Glu Thr Cys Glu Gln Ala Ser Thr Glu Ser Ala
615                 620                 625                 630 acc agg cat gct agc acc aag cct gaa ctc cca tcc cag aca gaa gcc    2155
Thr Arg His Ala Ser Thr Lys Pro Glu Leu Pro Ser Gln Thr Glu Ala
                635                 640                 645 att gag cag gcc agc act gag agt gct acc agg cat acc agt gcc aat    2203
Ile Glu Gln Ala Ser Thr Glu Ser Ala Thr Arg His Thr Ser Ala Asn
            650                 655                 660 cct gaa ctc cca tcc cag aca gaa gcc ata gca cct tta gct cat gaa    2251
Pro Glu Leu Pro Ser Gln Thr Glu Ala Ile Ala Pro Leu Ala His Glu
        665                 670                 675 gac cca tct gcc agg gac tct gct ctc cag gac aca gat gac agc gat    2299
Asp Pro Ser Ala Arg Asp Ser Ala Leu Gln Asp Thr Asp Asp Ser Asp
    680                 685                 690 gat gat ccg gtc ttg atc cct ggt gca aga tac cga aca gga cct ggt    2347
Asp Asp Pro Val Leu Ile Pro Gly Ala Arg Tyr Arg Thr Gly Pro Gly
695                 700                 705                 710 gat aga cgc tcc gct gtt gcc cgc att cag gag ttc ttc agg agg aga    2395
Asp Arg Arg Ser Ala Val Ala Arg Ile Gln Glu Phe Phe Arg Arg Arg
                715                 720                 725 aaa gaa agg aaa gaa atg gaa gag ctg gat act ttg aac att agg agg    2443
Lys Glu Arg Lys Glu Met Glu Glu Leu Asp Thr Leu Asn Ile Arg Arg
            730                 735                 740 cca cta gta aag atg gtt tat aag ggc cac cgc aac tcc cgg aca atg    2491
Pro Leu Val Lys Met Val Tyr Lys Gly His Arg Asn Ser Arg Thr Met
        745                 750                 755 ata aaa gaa gcc aat ttc tgg ggt gct aac ttt gta atg agc ggt tcc    2539
Ile Lys Glu Ala Asn Phe Trp Gly Ala Asn Phe Val Met Ser Gly Ser
    760                 765                 770 gat tgt ggc cat atc ttc atc tgg gac cgg cac act gcg gag cat ttg    2587
Asp Cys Gly His Ile Phe Ile Trp Asp Arg His Thr Ala Glu His Leu
```

```
                                                                         775                 780                 785                 790
atg ctt ctg gaa gct gat aat cat gtg gtc aac tgc ctg cag ccc cat          2635
Met Leu Leu Glu Ala Asp Asn His Val Val Asn Cys Leu Gln Pro His
            795                 800                 805 ccg ttt gac cca att cta gcc tca tct ggc ata gat tat gac ata aag          2683
Pro Phe Asp Pro Ile Leu Ala Ser Ser Gly Ile Asp Tyr Asp Ile Lys
        810                 815                 820 atc tgg tcg cca cta gaa gag tca aga att ttt aat cga aaa ctt gct          2731
Ile Trp Ser Pro Leu Glu Glu Ser Arg Ile Phe Asn Arg Lys Leu Ala
    825                 830                 835 gat gaa gtt ata act cgg aat gaa ctc acg ctg gaa gag act cgg aac          2779
Asp Glu Val Ile Thr Arg Asn Glu Leu Thr Leu Glu Glu Thr Arg Asn
        840                 845                 850 acc atc acc gtc cca gcc tct ttc atg ttg agg atg ttg gcg tca ctg          2827
Thr Ile Thr Val Pro Ala Ser Phe Met Leu Arg Met Leu Ala Ser Leu
855                 860                 865                 870 aat cat atc cga gct gac cgt ctg gag ggt gac aga tca gaa ggt tca          2875
Asn His Ile Arg Ala Asp Arg Leu Glu Gly Asp Arg Ser Glu Gly Ser
            875                 880                 885 ggt cag gag aat gaa aat gag gat gaa gaa taaagaactc cttggcaagc            2925
Gly Gln Glu Asn Glu Asn Glu Asp Glu Glu
        890                 895 acttagatgt tctgagattt gtatacgaca tttattatat ttttttttctt tacagaactt       2985 tagtgcaatt taaggctatg ggttttttttt tttctttttt tttggagttc ttccctattt       3045
tggggataac caaacattgg tttggaatga gtgtgtgcat gagttgggag agtgtgtaaa       3105
acaaagtaag caaaatgttt tttgaaacct tttgccgtgt atggagtccc aaaaaaaaaa       3165
aaaaaaaaaa aaaaaagcaa agtgcaatac ttcctgaccc tccgctgtgg gagcttggat       3225
caatgctgaa gtcattttca ttgtagtgaa aacgttggtt caaataaatt tctacacttg       3285
ccatttgcaa aaaaaaaaaa aaaaaaaaa aaaaaagcg gccgctgaat tctag              3340

<210> SEQ ID NO 4
<211> LENGTH: 896
<212> TYPE: PRT
<213> ORGANISM: Mus musculus

<400> SEQUENCE: 4

Met Ala Arg Ser Gly Ser Cys Pro His Leu Leu Trp Asp Val Arg Lys
1               5                   10                  15

Arg Ser Leu Gly Leu Glu Asp Pro Ser Arg Leu Arg Ser Arg Tyr Leu
            20                  25                  30

Gly Arg Arg Glu Phe Ile Gln Arg Leu Lys Leu Glu Ala Thr Leu Asn
        35                  40                  45

Val His Asp Gly Cys Val Asn Thr Ile Cys Trp Asn Asp Thr Gly Glu
    50                  55                  60

Tyr Ile Leu Ser Gly Ser Asp Asp Thr Lys Leu Val Ile Ser Asn Pro
65                  70                  75                  80

Tyr Ser Arg Lys Val Leu Thr Thr Ile Arg Ser Gly His Arg Ala Asn
            85                  90                  95

Ile Phe Ser Ala Lys Phe Leu Pro Cys Thr Asp Asp Lys Gln Ile Val
            100                 105                 110

Ser Cys Ser Gly Asp Gly Val Ile Phe Tyr Thr Asn Ile Glu Gln Asp
        115                 120                 125

Ala Glu Thr Asn Arg Gln Cys Gln Phe Thr Cys His Tyr Gly Thr Thr
    130                 135                 140
```

```
Tyr Glu Ile Met Thr Val Pro Asn Asp Pro Tyr Thr Phe Leu Ser Cys
145                 150                 155                 160

Gly Glu Asp Gly Thr Val Arg Trp Phe Asp Thr Arg Ile Lys Thr Ser
                165                 170                 175

Cys Thr Lys Glu Asp Cys Lys Asp Asp Ile Leu Ile Asn Cys Arg Arg
            180                 185                 190

Ala Ala Thr Ser Val Ala Ile Cys Pro Pro Val Pro Tyr Tyr Leu Ala
        195                 200                 205

Val Gly Cys Ser Asp Ser Ser Val Arg Ile Tyr Asp Arg Arg Met Leu
    210                 215                 220

Gly Thr Arg Ala Thr Gly Asn Tyr Ala Gly Arg Gly Thr Thr Gly Met
225                 230                 235                 240

Val Ala Arg Phe Ile Pro Ser His Leu Ser Asn Lys Ser Cys Arg Val
                245                 250                 255

Thr Ser Leu Cys Tyr Ser Glu Asp Gly Gln Glu Ile Leu Val Ser Tyr
            260                 265                 270

Ser Ser Asp Tyr Ile Tyr Leu Phe Asp Pro Lys Asp Asp Thr Ala Arg
        275                 280                 285

Glu Leu Lys Thr Pro Ser Ala Glu Glu Arg Arg Glu Glu Leu Arg Gln
    290                 295                 300

Pro Pro Val Lys Arg Leu Arg Leu Arg Gly Asp Trp Ser Asp Thr Gly
305                 310                 315                 320

Pro Arg Ala Arg Pro Glu Ser Glu Arg Arg Asp Gly Glu Gln Ser
                325                 330                 335

Pro Asn Val Ser Leu Met Gln Arg Met Ser Asp Met Leu Ser Arg Trp
            340                 345                 350

Phe Glu Glu Ala Ser Glu Val Ala Gln Ser Asn Arg Gly Arg Gly Arg
        355                 360                 365

Pro Arg Pro Arg Gly Gly Thr Asn Gln Pro Asp Val Ser Thr Leu Pro
    370                 375                 380

Thr Val Pro Ser Ser Pro Asn Leu Glu Val Cys Glu Thr Ala Met Asp
385                 390                 395                 400

Val Asp Met Pro Ala Ala Leu Leu Gln Pro Ser Thr Ser Ser Thr Asp
                405                 410                 415

Pro Val Gln Ala Gln Ala Ala Thr Ala Ala Ile Glu Ser Pro Arg Ser
            420                 425                 430

Ser Ser Leu Leu Ser Cys Pro Asp Ser Glu Pro Arg Gln Ser Val Glu
        435                 440                 445

Ala Ser Gly His His Ala His His Gln Ser Asp Ser Pro Ser Ser Val
    450                 455                 460

Val Asn Lys Gln Leu Gly Ser Met Ser Leu Asp Glu Gln Gln Asp Asn
465                 470                 475                 480

Ser Asn Glu Arg Leu Ser Pro Lys Pro Gly Thr Gly Glu Pro Val Leu
                485                 490                 495

Ser Leu His Tyr Ser Thr Glu Gly Thr Thr Ser Thr Ile Lys Leu
            500                 505                 510

Asn Phe Thr Asp Glu Trp Ser Ser Thr Ala Ser Ser Ser Arg Gly Asn
        515                 520                 525

Gly Ser His Cys Lys Ser Glu Gly Gln Glu Glu Cys Leu Val Pro Pro
    530                 535                 540

Ser Ser Val Gln Pro Pro Glu Gly Asp Ser Glu Thr Arg Ala Pro Glu
545                 550                 555                 560

Glu Leu Ser Glu Lys Gly Thr Leu Pro Glu Asn Leu Thr Gln Asn Gln
```

565                 570                 575
Ile Asp Thr Ala Gln Leu Asp Asn Phe Pro Ala Glu Pro Leu Asp Ser
            580                 585                 590

Asn Ser Gly Glu Lys Asn Asn Pro Ser Gln Asp Ser Pro Cys Gly Leu
            595                 600                 605

Pro Glu Glu Gly Thr Leu Ser Glu Thr Asp Arg Glu Thr Cys Glu Gln
    610                 615                 620

Ala Ser Thr Glu Ser Ala Thr Arg His Ala Ser Thr Lys Pro Glu Leu
625                 630                 635                 640

Pro Ser Gln Thr Glu Ala Ile Glu Gln Ala Ser Thr Glu Ser Ala Thr
                645                 650                 655

Arg His Thr Ser Ala Asn Pro Glu Leu Pro Ser Gln Thr Glu Ala Ile
                660                 665                 670

Ala Pro Leu Ala His Glu Asp Pro Ser Ala Arg Asp Ser Ala Leu Gln
                675                 680                 685

Asp Thr Asp Asp Ser Asp Asp Pro Val Leu Ile Pro Gly Ala Arg
    690                 695                 700

Tyr Arg Thr Gly Pro Gly Asp Arg Arg Ser Ala Val Ala Arg Ile Gln
705                 710                 715                 720

Glu Phe Phe Arg Arg Lys Glu Arg Lys Glu Met Glu Glu Leu Asp
                725                 730                 735

Thr Leu Asn Ile Arg Arg Pro Leu Val Lys Met Val Tyr Lys Gly His
                740                 745                 750

Arg Asn Ser Arg Thr Met Ile Lys Glu Ala Asn Phe Trp Gly Ala Asn
            755                 760                 765

Phe Val Met Ser Gly Ser Asp Cys Gly His Ile Phe Ile Trp Asp Arg
    770                 775                 780

His Thr Ala Glu His Leu Met Leu Leu Glu Ala Asp Asn His Val Val
785                 790                 795                 800

Asn Cys Leu Gln Pro His Pro Phe Asp Pro Ile Leu Ala Ser Ser Gly
            805                 810                 815

Ile Asp Tyr Asp Ile Lys Ile Trp Ser Pro Leu Glu Glu Ser Arg Ile
            820                 825                 830

Phe Asn Arg Lys Leu Ala Asp Glu Val Ile Thr Arg Asn Glu Leu Thr
        835                 840                 845

Leu Glu Glu Thr Arg Asn Thr Ile Thr Val Pro Ala Ser Phe Met Leu
    850                 855                 860

Arg Met Leu Ala Ser Leu Asn His Ile Arg Ala Asp Arg Leu Glu Gly
865                 870                 875                 880

Asp Arg Ser Glu Gly Ser Gly Gln Glu Asn Glu Asn Glu Asp Glu Glu
                885                 890                 895

HUMAN ARCAP TRANSGENIC MOUSE

BACKGROUND

The human Androgen Receptor Complex Associated Protein (ARCAP) gene was first isolated via a yeast two-hybrid assay using the androgen receptor ligand-binding domain as bait. The human ARCAP mRNA has an open reading frame of 2583 nucleotides that encodes 860 amino acids with a calculated molecular weight of 95 Kd. See U.S. Pat. Nos. 6,974,683 and 7,083,935, as well as NCBI accession No DQ768089. Analysis of the human ARCAP gene revealed that it includes 19 exons over 135 kb of genomic DNA at chromosome 1q23.2-q24.3 region.

Studies have shown that the human ARCAP gene is expressed in hepatoma cell lines but not in normal human liver cells. See U.S. Pat. Nos. 6,974,683 and 7,083,935.

The role of ARCAP in the development of hepatomas is not currently understood.

Hepatoma formation is a complex process. The need exists to develop animal models for investigating morphological and molecular lesions leading to the transition of normal liver tissue into liver tumors.

SUMMARY

To meet the needs set forth above, provided herein is a non-human transgenic animal that contains in its genome a nucleic acid encoding human ARCAP operably linked to a liver-specific promoter. The transgenic animal expresses the human ARCAP protein and develops tumors of the liver, spleen, abdomen, or lymph.

Also provided is a cell line derived from the non-human transgenic animal expressing the human ARCAP gene.

In addition, a method for producing a transgenic mouse is disclosed. The method includes (i) micro-injecting into a fertilized mouse oocyte a vector that contains a human ARCAP cDNA operably linked to a liver-specific promoter and (ii) transferring the micro-injected mouse oocyte into a foster mouse to produce a transgenic mouse that expresses human ARCAP. The transgenic mouse develops liver, spleen, abdomen, or lymph tumors.

The details of one or more embodiments are set forth in the description and the examples below. Other features, objects, and advantages will be apparent from the detailed description of several embodiments and also from the claims. All publications and patent documents cited herein are incorporated by reference in their entirety.

BRIEF DESCRIPTION OF THE DRAWINGS

The description below refers to the accompanying drawings, of which:

FIG. 3 shows an alignment between the amino acid sequences of the human ARCAP protein (H; SEQ ID NO: 2) and the murine ARCAP protein (M; SEQ ID NO: 4).

DETAILED DESCRIPTION

Figure 1A:
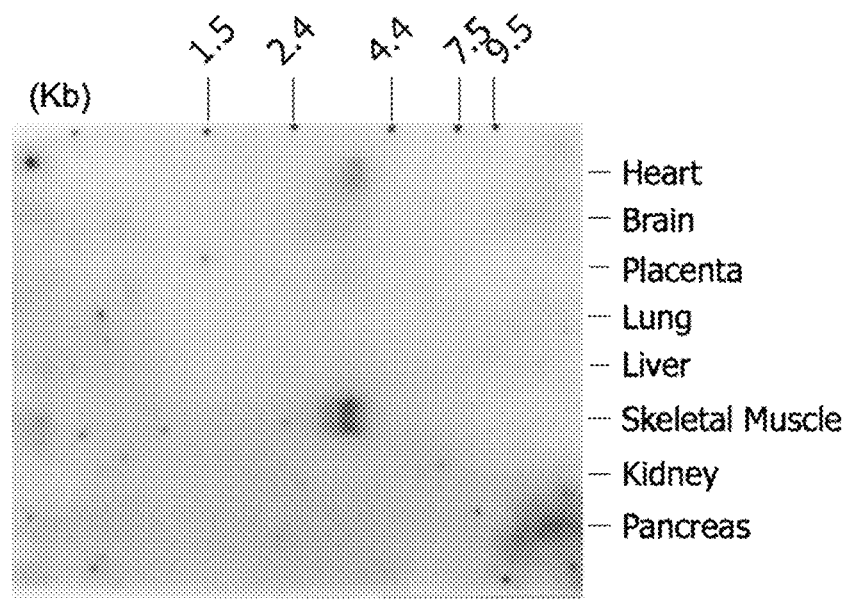
FIG. 1A shows an autoradiogram of a Northern blot analysis of human ARCAP mRNA in human tissues.

As mentioned above, a non-human transgenic animal expressing human ARCAP is disclosed herein. The non-human transgenic animal can be a mammal. For example, the non-human transgenic animal can be a primate, ungulate, canine, murine, or feline. In a specific embodiment, the non-human transgenic animal is a mouse.

The transgene includes a nucleic acid encoding human ARCAP operably linked to a liver-specific promoter. The liver-specific promoter can be, but is not limited to, an albumin promoter or a phosphoenolpyruvate carboxykinase (PEPCK) promoter.

The nucleic acid encoding the human ARCAP protein can encode the amino acid sequence of SEQ ID NO: 2 or an amino acid sequence 75% to 95% (e.g., 75%, 80%, 85%, 90%, 95%) identical to SEQ ID NO 2.

The murine ARCAP protein (SEQ ID NO: 4) shares 83% amino acid identity with the human ARCAP protein. See FIG. 5. A nucleic acid encoding the murine ARCAP protein (see e.g., SEQ ID NO: 3) falls outside the scope of the application.

The nucleic acid that encodes the human ARCAP protein can include the sequence of SEQ ID NO: 1 or a sequence 75% to 99% identical to SEQ ID NO: 1. In a specific embodiment, the nucleic acid encoding human ARCAP includes the sequence of SEQ ID NO: 1.

The transgenic animal described above expresses the human ARCAP protein and develops tumors of the liver, spleen, abdomen, or lymph. Tumors can be identified in these animals pathologically at approximately four months of age.

Transgenic mice expressing the murine ARCAP protein, unlike those expressing the human ARCAP protein, do not develop tumors.

A cell line derived from the non-human transgenic animal described, supra, can be isolated from any tissue. In certain embodiments, the cell line is derived from the liver, spleen, abdomen, or lymph tumor.

Moreover, the method for producing a transgenic mouse set forth above includes a step of micro-injecting into a fertilized mouse oocyte a vector that contains a human ARCAP cDNA operably linked to a liver-specific promoter.

The human ARCAP cDNA can encode the amino acid sequence of SEQ ID NO: 2 or an amino acid sequence 75% to 95% (e.g., 75%, 80%, 85%, 90%, 95%) identical to SEQ ID NO 2. Again, a nucleic acid encoding the murine ARCAP protein (SEQ ID NO: 4) falls outside the scope of the application.

The human ARCAP cDNA can include the sequence of SEQ ID NO: 1 or a sequence 75% to 99% identical to SEQ ID NO: 1. In a specific embodiment, the human ARCAP cDNA includes the sequence of SEQ ID NO: 1.

The human ARCAP cDNA is operably linked to a liver-specific promoter, e.g., the murine albumin promoter or the murine PEPCK promoter.

The micro-injected mouse oocytes are transferred into a foster mouse to produce a transgenic mouse that expresses human ARCAP. The transgenic mouse develops liver, spleen, abdomen, or lymph tumors.

Again, transgenic mice expressing the murine ARCAP protein do not develop tumors.

Without further elaboration, it is believed that one skilled in the art can, based on the disclosure herein, utilize the present disclosure to its fullest extent. The following specific examples are, therefore, to be construed as merely descriptive, and not limitative of the remainder of the disclosure in any way whatsoever.

EXAMPLES

Example 1

Expression of Human ARCAP

Northern blot analysis was performed to assess expression of human ARCAP mRNA in tissues. The results are shown in FIG. 1A. Human ARCAP mRNA is weakly expressed in heart and skeletal muscle. It is not expressed in most normal human tissues, including normal liver tissue.

Figure 1B:
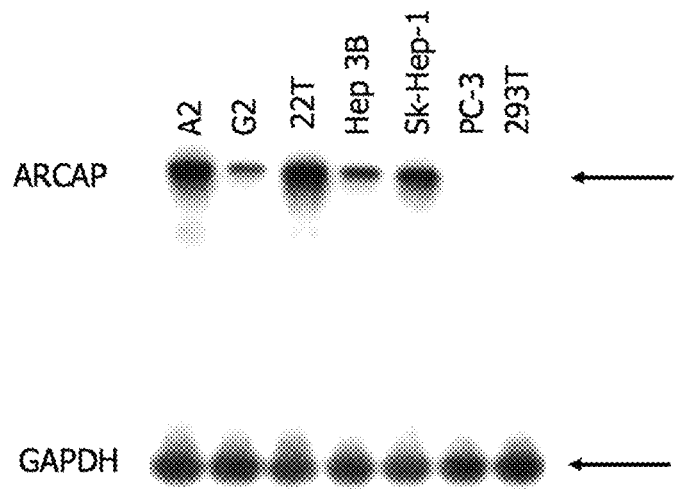
FIG. 1B shows an autoradiogram of a Northern blot analysis of human ARCAP mRNA in the indicated cell lines. A2, G2, 22T, Hep3B, Sk-Hep-1 are human hepatoma cell lines, PC-3 is a human prostate cancer cell line, and 293T is an immortalized human embryonic kidney cell line. Glyceraldehyde phosphate dehydrogenase (GAPDH) expression was measured as an internal control.

Human ARCAP mRNA expression was examined in cultured hepatoma cell lines. The results, shown in FIG. 1B, indicated that ARCAP is highly expressed in human hepatoma cell lines but not in prostate cancer cells or kidney cells.

Figure 1C:
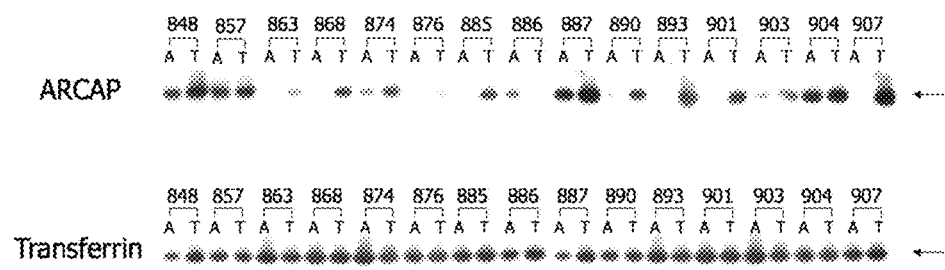
FIG. 1C shows Northern blot analysis of human ARCAP mRNA and transferrin control in paired tissues from human liver tumor tissue (T) and adjacent normal tissue (A)

Expression of human ARCAP mRNA was also examined in paired tissue samples from patients suffering from hepatocellular carcinoma. The results are shown in FIG. 1C. Human ARCAP was expressed at significantly higher levels in 13 out of 15 hepatocellular carcinoma tissue samples tested as compared to adjacent normal liver tissue. This data suggests that human ARCAP plays a role in tumorigenesis, particularly in the liver.

Example 2

Overexpression of Human ARCAP Induces a Cancerous Phenotype in Normal Liver Cells Permanent Transfection of Normal Liver Cells The 2.8 kb full-length human ARCAP cDNA was cloned into vector pLXSN and used to transfect normal murine liver BNL cells. In brief, BNL cells were grown at 37° C. in 10% $CO_2$. Plasmid DNA constructs mixed with Lipofectamine 2000 and media were added to the cells upon reaching 60-70% confluence. The media was replaced with fresh media after 24 h. Geneticin (G418) was added to the media to select stable transfectants. BNL cells were transfected with pLXSN-ARCAP and selected with G418 to establish permanently transfected cells that overexpress human ARCAP (BNL-ARCAP). Control cells were transfected with empty plasmid pLXSN and subjected to selection to create BNL-pLXSN cells. The expression of human ARCAP in the BNL cells was evaluated for its effects on cell migration, cell invasion, and anchorage-independent clonal growth.

In Vitro Wound Healing Assay

An in vitro wound healing assay was used to measure cell migration rates on a tissue culture surface. This assay mimics cell migration during wound healing in vivo. It is particularly suitable for studies of the effects of cell-matrix and cell-cell interactions on cell migration.

BNL cells, BNL-pLXSN cells, and BNL-ARCAP cells were each grown to confluence as a monolayer in a tissue culture flask. The surfaces of the monolayers were gently and slowly scratched with a 200 µl pipette tip to create an area devoid of cells. Cell growth and migration into the area devoid of cells was observed under a microscope and photographs taken periodically. Image analysis software (Image J) was used to measure the size of the area free of cells. The results are shown in Table 1 below.

TABLE 1

| | Wound healing assay | | |
|---|---|---|---|
| Cells | 6 h[a] | 24 h | 48 h |
| BNL | 0.6[b] | 0.4 | 0.2 |
| BNL-pLXSN | 0.6 | 0.4 | 0.2 |
| BNL-ARCAP | 0.4 | 0.2 | 0.1 |

[a]time elapsed after scratching cell monolayer
[b]fold change in size of cell-free area. All values for BNL-ARCAP cells were significantly different from the corresponding values for both BNL and BNL-pLXSN cells p < 0.05.

BNL cells overexpressing human ARCAP more quickly and completely filled in the area devoid of cells as compared to un-transfected BNL cells or BNL-pLXSN cells.

Cell Migration Assay

A trans-well tissue culture chamber was prepared by coating the upper trans-wells with poly-L-lysine. BNL, BNL-pLXSN, and BNL-ARCAP cells were seeded into separate upper trans-wells at a cell density of $1\times10^5$ cells per well. The trans-well chamber was incubated at 37° C. in 10% $CO_2$.

After growing the cells for 24 h, the media was removed from the upper trans-well. Cells remaining in the upper well and those that migrated to the bottom well were fixed with 4% paraformaldehyde at room temperature for 10 min. Fixed cells were rinsed 3 times with PBS and then incubated with 100% methanol for 10 min. After washing with PBS, 0.05% Crystal Violet was added for 10 min. to stain the cells. The numbers of cells in the upper and lower trans-wells were observed via microscope and counted. The results are shown in Table 2 below.

TABLE 2

| | Trans-well cell migration assay | | | | |
|---|---|---|---|---|---|
| Cells | Exp. 1 | Exp. 2 | Exp. 3 | mean | ±S.D.[b] |
| BNL | 10[a] | 13 | 21 | 15 | 5.69 |
| BNL-pLXSN | 11 | 19 | 25 | 18[c] | 7.02 |
| BNL-ARCAP | 123 | 163 | 159 | 148[d] | 22.03 |

[a]values are number of cells counted in the lower trans-well
[b]standard deviation from the mean
[c]BNL vs. BNL-pLXSN not significantly different p = 0.128
[d]BNL vs. BNL-ARCAP significantly different p = 0.0066

BNL-ARCAP cells demonstrated significantly more cell migration across the trans-well as compared to BNL and BNL-pLXSN cells.

Soft Agar Colony Formation Assay

The soft agar colony formation assay is used to quantify anchorage-independent cell growth in vitro. Anchorage-independent growth of cells correlates with their tumorigenic potential.

Individual wells of a tissue culture plate were prepared with a base agar and a top agar following standard procedures. Each well was seeded with $1\times10^4$ cells (HepG2, BNL, BNL-pLXSN, and BNL-ARCAP) in media and placed in an incubator at 37° C. in 10% $CO_2$. The media was changed every three days for 21-28 days. Cell colonies in each well were stained with 0.005% Crystal Violet and washed with PBS. Cell colonies were observed by microscopy and counted. The results are shown in Table 3 below.

TABLE 3

Soft agar colony formation assay

| Cells | Exp. 1 | Exp. 2 | Exp. 3 | mean | ±S.D.[b] |
|---|---|---|---|---|---|
| BNL | 19[a] | 20 | 13 | 17 | 3.785939 |
| BNL-pLXSN | 33 | 41 | 38 | 37[c] | 4.041452 |
| BNL-ARCAP | 368 | 377 | 361 | 369[d] | 8.020806 |
| HepG2 | 236 | 223 | 230 | 230 | 6.506407099 |

[a]values are number of colonies formed
[b]standard deviation from the mean
[c]BNL vs. BNL-pLXSN significantly different p = 0.025
[d]BNL vs. BNL-ARCAP significantly different p = 6.57 × 10$^{-5}$ BNL-ARCAP cells showed the highest degree of anchorage-independent growth among the cells tested. HepG2 human hepatoma cells tested in the assay formed approximately two-thirds the number of colonies as did BNL-ARCAP cells. Control BNL and BNL-pLXSN cells did not form large numbers of colonies in this assay.

Example 3

Transgene Constructs

Figure 2A:
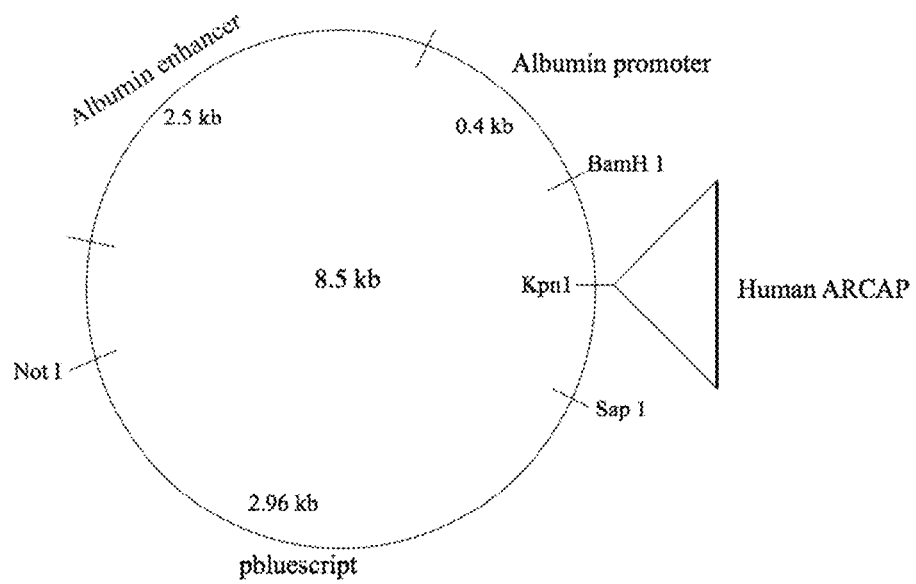
FIG. 2A is a diagram of a plasmid construct for generating human ARCAP transgenic animals. The construct includes the murine albumin promoter and the human ARCAP cDNA.

The 2.8 Kb full length human ARCAP cDNA was subcloned using standard techniques into an expression vector downstream of the mouse albumin promoter. See FIG. 2A. The resulting 5.8 Kb albumin promoter/ARCAP construct was digested with Not I and Sap I prior to microinjection.

Figure 2B:
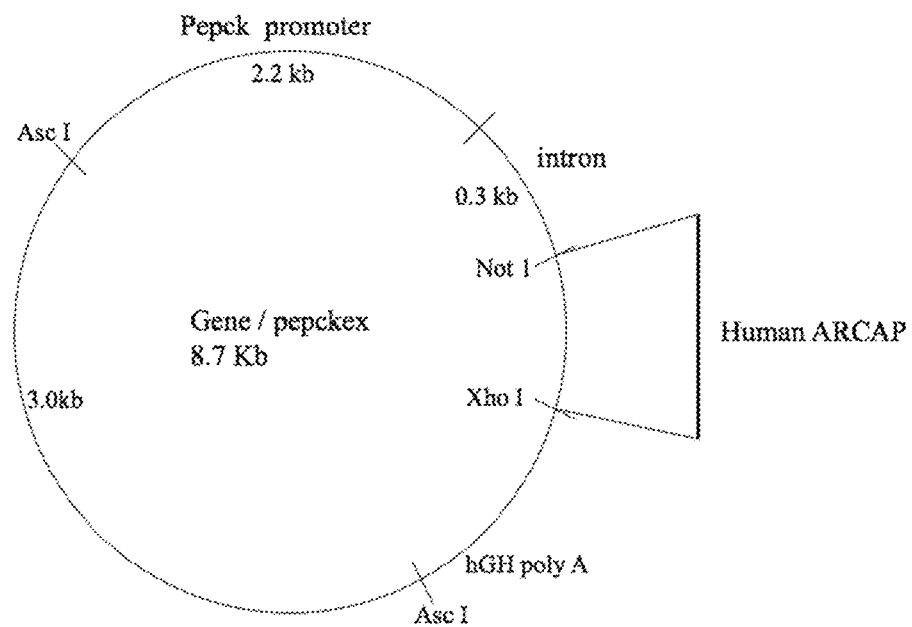
FIG. 2B is a diagram of an alternative plasmid construct for generating human ARCAP transgenic animals. The construct includes the murine phosphoenolpyruvate carboxykinase (PEPCK) promoter and the human ARCAP cDNA.

The ARCAP cDNA was also cloned into an expression vector downstream of the mouse PEPCK promoter. See FIG. 2B. The resulting 5.7 Kb PEPCK promoter/ARCAP construct was digested with Asc I prior to microinjection.

Example 4

Pronuclear Microinjection

ARCAP containing DNAs were microinjected into fertilized C57/BL6J female embryos (0.5 dpc embryos) at the Taiwan Animal Center (Taipei, Taiwan). The injected zygotes were transferred back to foster mice mothers according to standard protocols. Transgenic mice were generated and housed under standard specific pathogen free conditions. All animal studies were conducted in accordance with the rules established by the Institutional Animal Care and Use Committee at the institute of Taipei-Veterans General Hospital animal facility.

Example 5 hARCAP Expressing Transgenic Mice Develop Tumors

Twenty transgenic mice expressing human ARCAP from the albumin promoter and 20 mice expressing human ARCAP from the albumin promoter were analyzed. All 40 mice developed tumors within 3 months after birth.

Importantly, 10 transgenic mice each overexpressing the murine ARCAP gene under the control of a liver-specific promoter have been tumor-free for as long as two years.

RT-PCR analysis was performed on human ARCAP transgenic mice RNA samples extracted from normal liver, abnormal liver, liver tumor, abdominal tumor, normal blood, abnormal blood, normal spleen, enlarged spleen, and spleen tumor. Normal tissues appeared histologically normal. The results are shown in Table 4 below. Abnormal tissues showed pathologic changes but no frank tumors. For example, normal liver showed expected liver histology. Abnormal liver displayed abnormal color, slight enlargement, and the appearance of nodules. Tumor samples were confirmed as malignant by histology.

TABLE 4

Relative mRNA expression in human ARCAP transgenic mouse tissues

| Tissue | ARCAP | CD3 | CD20 | CK19 | AR | TAT | AFP |
|---|---|---|---|---|---|---|---|
| Normal liver | 1 | 1 | 1 | 1 | 1 | 1 | 1 |
| Abnormal liver | 0.5 | 0.03* | 1.2* | 4.2* | 0.8 | 1.0 | 0.9 |
| Liver tumor | 1.6* | 1.5* | 0.9* | 2.9* | 1.6* | 1.3* | 3.9* |
| Abdominal tumor | 1.0 | 0.3* | 2.2* | 9.1* | 0.4* | 1.3* | 1.1 |
| Normal blood | 1.3* | 0.8* | 0.9 | 2.5* | 0.95 | 0.1* | 0.9 |
| Abnormal blood | 2.3* | 1.2 | 0.7* | 4.8* | 1.2 | 0.1* | 6.3* |
| Normal spleen | 1[a] | 1 | 1 | 1 | 1 | 1 | 1 |
| Enlarged spleen | 1.2* | 1.3* | 1.1 | 1.0 | N.D. | 1.2* | 4* |
| Spleen tumor | 1.7* | 1.4* | 2.1* | 1.5* | N.D. | 2.7* | 7.5* |

[a]spleen tissue RNA expression levels are relative to normal spleen
*significantly different from normal liver or normal spleen p < 0.05

The data revealed that ARCAP was highly expressed in liver, spleen, and abdominal tumors in albumin promoter/human ARCAP transgenic mice. Elevated expression of cytokeratin 19 (CK19; a marker of cell proliferation), tyrosine amino transferase (TAT; associated with hepatitis), and alpha-fetoprotein (AFP; a marker of liver cancer) was also observed. See Table 4, supra.

In PEPCK promoter/ARCAP transgenic mice, RT-PCR analysis also showed high levels of ARCAP expression in spleen tumor tissues. See Id. High levels of CDK19, TAT, and AFP were also noted, particularly in abdominal tumors.

Further, all human ARCAP transgenic mice were free of Hepatitis B virus and Hepatitis C virus infection.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, a person skilled in the art can easily ascertain the essential characteristics of the present disclosure, and without departing from the spirit and scope thereof, can make various changes and modifications of the present disclosure to adapt it to various usages and conditions. Thus, other embodiments are also within the claims.

The invention claimed is:

1. A transgenic mouse comprising in its genome a nucleic acid encoding human Androgen Receptor Complex Associated Protein (ARCAP) operably linked to a liver-specific promoter, wherein the transgenic mouse expresses the human ARCAP protein and develops a liver, spleen, abdomen, or lymph tumor.

2. The transgenic mouse of claim 1, wherein the liver-specific promoter is the murine albumin promoter or the murine phosphoenolpyruvate carboxykinase (PEPCK) promoter.

3. The transgenic animal mouse of claim 1, wherein the nucleic acid includes the sequence of SEQ ID NO: 1.

4. The transgenic mouse of claim 2, wherein the nucleic acid includes the sequence of SEQ ID NO: 1.

5. A cell line derived from the transgenic mouse of claim 1.

6. The cell line of claim 5, wherein the cell line is derived from the liver, spleen, abdomen, or lymph tumor.

7. A cell line derived from the transgenic mouse of claim 2.

8. The cell line of claim 7, wherein the cell line is derived from the liver, spleen, abdomen, or lymph tumor.

9. A method for producing a transgenic mouse, the method comprising:
micro-injecting into a fertilized mouse oocyte a vector that contains a human Androgen Receptor Complex Associated Protein (ARCAP) cDNA operably linked to a liver-specific promoter, and transferring the micro-injected mouse oocyte into a foster mouse, thereby producing a transgenic mouse that expresses human ARCAP, wherein the transgenic mouse develops a liver, spleen, abdomen, or lymph tumor.

10. The method of claim 9, wherein the liver-specific promoter is the murine albumin promoter or the murine phosphoenolpyruvate carboxykinase (PEPCK) promoter.

11. The method of claim 10, wherein the cDNA includes the sequence of SEQ ID NO: 1.

* * * * *